United States Patent [19]

Martin

[11] Patent Number: 5,618,302

[45] Date of Patent: Apr. 8, 1997

[54] MALE URETHRAL CLOSURE PAD

[76] Inventor: Wallace K. Martin, 1221 Sarasota Dr., Tallahassee, Fla. 32301

[21] Appl. No.: 418,674

[22] Filed: Apr. 7, 1995

[51] Int. Cl.$^6$ .................................................. A61B 17/00
[52] U.S. Cl. ........................ 606/201; 128/DIG. 25; 128/1; 602/61
[58] Field of Search .................... 606/201, 202, 606/203; 128/DIG. 25, 1, 346, 326, 327, 79

[56] References Cited

U.S. PATENT DOCUMENTS

| 2,756,753 | 7/1956 | Means | 128/DIG. 25 |
| 4,534,353 | 8/1985 | de Leur et al. | 128/DIG. 25 |
| 4,800,900 | 1/1989 | French | 128/DIG. 25 |

FOREIGN PATENT DOCUMENTS

| 2717924 | 10/1978 | Germany | 128/DIG. 25 |

Primary Examiner—Michael Powell Buiz
Assistant Examiner—Kevin Truong
Attorney, Agent, or Firm—Carnes Cona and Dixon

[57] ABSTRACT

The present invention provides a male urethral closure pad or clamp device that is designed to stop or minimize the involuntary loss of urine in men. The male urethral closure pad or clamp device of the present invention consists of a first strap and a second strap. The first strap includes a first end and a second end. Centrally located on the inside surface of the first strap is an inclusion pad. The second pad is fabricated from an elastic like material and is secured to the outside surface of the first strap. Utilization of the device occurs when the inclusion pad is placed under the urethra canal. This will enable the first end and the second end to wrap around the penis to render for the first end to overlap the second end. The second strap is wrapped completely around and is secured to the first strap via a securing member.

16 Claims, 4 Drawing Sheets

MALE URETHRAL CLOSURE PAD

BACKGROUND OF THE INVENTION

1. Field of the Invention

The present invention relates generally to a male urethral closure pad, and more particularly to a closure pad that will stop or minimize the involuntary loss of urine in men by placing pressure on the penile urethra canal.

2. Description of the Prior Art

Incontinence occurs in men under various circumstances such as, but not limited to, the process of aging or prostrate surgery. Whatever the cause, it is a source of embarrassment and discomfort. Attempts have been made to provide relief from the condition in the form of clamping devices. These clamping devices are designed to provide pressure on the penile urethra canal and have been successful in preventing the flow of urine. However, these devices are bulky, uncomfortable, difficult to use, hard to clean and visually obvious when worn. Accordingly, efforts have been made to improve the traditional clamps in order to make the clamps easier to use and more comfortable to wear.

Such a device is disclosed in U.S. Pat. No. 2,756,753 issue to Means. Means discloses a device that is adapted to be secured around the penis to provide for a pad to apply pressure on the urethra canal. The device consists of an elastic strap having a first end and a second end. The pad is located on this elastic strap. Located at the second end is a clamping mechanism that is adapted to receive the first end. This device, though somewhat efficient, does suffer some drawbacks. The clamping mechanism used by Means is bulky, and as such provides for a device that is uncomfortable to wear. Further, the combination of the clamping mechanism and the use of a single strap provides for a device that is difficult to maneuver and secure onto the penis. Additionally, the use of the clamping mechanism provides for a device that is virtually impossible to be washed, hence rendering a device that is potentially non hygienic.

A second device is disclosed in German Patent DT 2717-924 issue to Sachse. Sachse discloses a strap that includes a pad located on a top surface of the strap. The strap further includes a first end, a second end, and a slit which located in the proximity of the pad. This slit is adapted to receive either the first end or second end of the strap for enabling the strap to be secured around the penis, thereby rendering for the pad to be located under the urethra canal. The use of the slit provides for a device that is difficult and tedious to use, especially for the elderly, men with poor eye sight, and for individuals who are arthritic. The attempt to insert an end of the strap into the slit provides for a device that is laborious to manipulate and extremely time consuming to secure to the penis. Additionally, with time it appears that this slit would easily tear, thereby rendering a device that is useless. Still further, a first engaging material is located in the proximity of the slit. An end of the strap is received in the slit, while the opposite end is provided with a second engaging material that is adapted to engage and contact the first engaging material. This particular design and configuration will add only to the awkwardness of the device rather than to the simplicity; due to the user having to maneuver the end which is received in the slit in order to permit for the opposite end to engage the engaging material. Accordingly, the design of this strap provides for an end to inherently block the engaging material, thereby adding to the difficulty of the utility of the device.

None of these previous efforts, however, provide the benefits intended with the present invention, such as providing a closure pad device that is effective, comfortable, easy to use, and is hygienically washable. Additionally, prior techniques do not suggest the present inventive combination of component elements as disclosed and claimed herein. The present invention achieves its intended purposes, objectives and advantages over the prior art by providing a device that will minimize or eliminate the flow of urine by placing pressure on the penile urethra canal through a new, useful and unobvious combination of component elements. The device of the present invention is simple to use and is inexpensive to manufacture and assemble. Additionally, the present invention employs only readily available material.

SUMMARY OF THE INVENTION

The present invention provides a device that will stop or minimize the involuntary flow of urine in males by placing pressure on the penile urethra canal. This device is comfortable to wear and easy to utilize.

The urethral closure pad or clamping device of the present invention consists of a first strap made of a soft padded material, such as but not limited to reinforced polyurethane foam. This first strap includes a first end portion, a central portion and a second end portion. On the inside surface of the center portion of the first strap is an inclusion pad. The inclusion pad extends upwardly from the inside surface. This inclusion pad is fabricated from a rigid material. It is this pad that is used to transmit pressure on the penile urethra canal, inherently blocking or stopping the flow of urine. This pad can be covered with a soft material, such as but not limited to cotton felt. Centrally located on the outside surface of the first strap and oppositely from the pad is a first engaging material, such as hook or loop material (VELCRO).

A second strap, having a first end and a second end, is made from an elastic or flexible material. The first end of the second strap is secured to the first strap in the proximity of the first engaging material. Located on a bottom surface of the second strap is a second engaging material.

Utilization of the device of the present invention occurs by centrally placing the first strap on the under surface of the penis, so as to provide for the inclusion pad to be under the urethra canal. With the inclusion pad in place on the under surface of the penis, the first end of the first strap is wrapped around the penis. The second end of the first strap is overlapped onto the first end of the first strap. The second strap is then stretched around and over the first and second ends of the first strap to provide for the second engaging material the second end of the second strap to engage the first engaging material that is located centrally on the bottom surface of the first strap. This second strap would be stretched enough in order to place pressure on the penile urethra canal via the inclusion pad but still not tight enough to stop blood circulation. Hence the device of the present invention places pressure directly on the urethra canal in order to provide a means of closing the canal to inherently stop the flow of urine.

Accordingly, it is the object of the present invention to provide an urethral closure pad that will be effective in stopping the flow of urine in male by placing pressure on the penile urethra canal.

It is another object of the present invention to provide an urethral closure pad that is comfortable to wear and easy to utilize and hygienically clean.

Still another object of the present invention is to provide an urethral closure pad that will prevent the user from locking or securing the device too tightly and to also provide an urethral closure pad that is not irritating for the user.

Yet another object of the present invention is to provide an urethral closure pad that with continual use will inherently permit for the user's bladder to return to its normal or near normal capacity.

A final object of the present invention, to be specifically enumerated herein, is to provide a clamp device in accordance with the preceding objects and which will conform to conventional forms of manufacture and be of simple construction so as to provide a device that would be economically feasible, long lasting and relatively trouble free in operation.

Although there have been many inventions related to a clamp device to stop or minimize the flow of urine, none of the inventions have become sufficiently compact, low cost, and reliable enough to become commonly used. The present invention meets the requirements of the simplified design, compact size, low initial cost, ease of utilization and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Thereby, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

Similar reference numerals refer to similar parts throughout the several views of the drawings.

DESCRIPTION OF THE PREFERRED EMBODIMENTS

Figure 1:
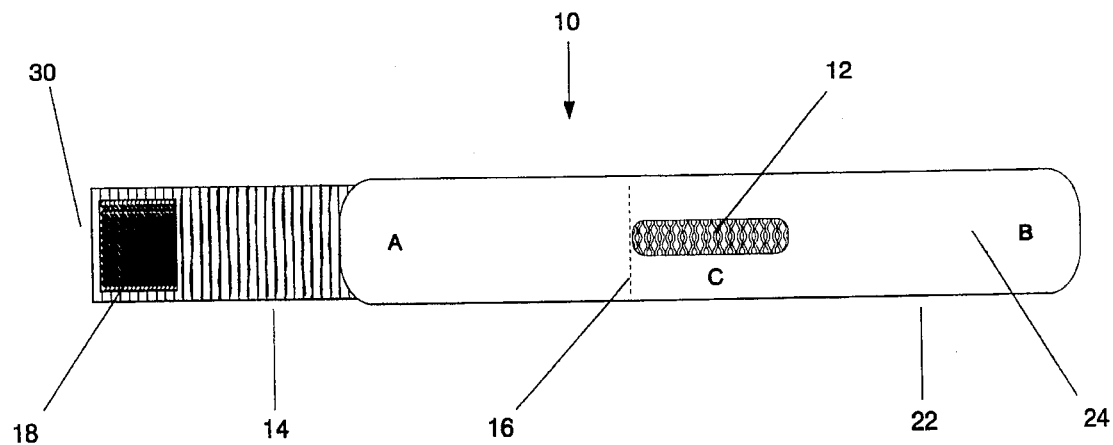
FIG. 1 is an inside plan view of the urethral closure pad of the present invention.
Figure 2:
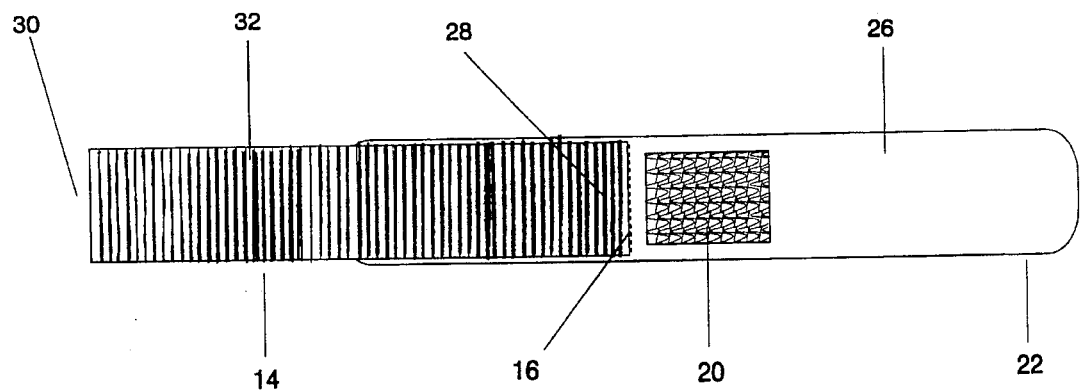
FIG. 2 is an outside plan view of the urethral closure pad of the present invention.
Figure 3:
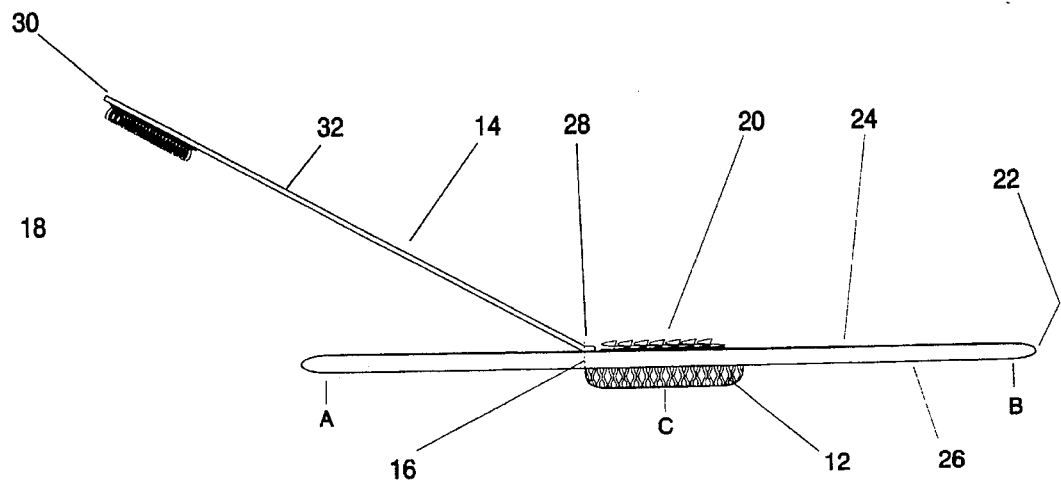
FIG. 3 is a side view of the urethral closure pad of the present invention.

FIGS. 1–3 illustrate the various views of the clamp device or the male urethral pad of the present invention. As seen in these figures, the urethral closure pad 10 of the present invention, includes a first strap 22 and a second strap 14. The first strap 22 consists of three sections, a first end or segment tab portion portion A, a center C, and a second end or segment tab B. Centrally located on the inside surface 24 of the first strap 22 is an inclusion pad 12.

The first strap of the male urethra closure pad 10 can be fabricated from a variety of materials. It is noted that polyurethane foam reinforced with a bonded napped nylon or cotton has been utilized to produce excellent results. Other material of a varying degree of flexibility may also be utilized. These materials include, but are not limited to, canvas, cotton, neoprene/vinyl/SBR, foam neoprene rubber, or any close cell foams, resilient and breathable material.

This inclusion pad 12 is fabricated from a rigid material such as plastic. Optionally, the inclusion pad 12 can be coated, padded, or covered with a soft material, such as, but not limited to cotton, felt, or cotton felt. The ends of the inclusion pad 12 may be beveled (see FIG. 3). These beveled ends of the inclusion pad will enable the inside surfaces of the first end A and the second end B to contact the beveled ends so as to provide the first and second straps to contour nicely and comfortably around the penis.

Centrally located on the outside surface 26 of the first strap 22 is the first securing means 20. As illustrated in FIG. 1, the first securing means 20 includes an interlocking material, such as engaging fabric hook or loop material (VELCRO).

To eliminate the possibility of the user from attaching the male urethral pad 10 too tightly onto the penis, the first securing means 20 on the outside surface is located directly, centrally, and oppositely from the inclusion pad 12.

It is noted, that this first securing means is not needed if the first strap is bonded with a napped nylon material. This nylon material will inherently provide engaging means for the second securing means 18 which is located on the second strap 14.

The second strap 14 is fabricated from an elastic-like or flexible material and includes a first end 28, a second end 30, a lower surface 32, and a top surface 34. The first end 28 of the second strap 14 is secured to the first strap 22 at a securment point 16. This securment can be any conventional securment means, such as, but not limited to the use of adhesives or sewing.

This first end 28 of the second strap 14 is secured to the outside surface of the first strap, in the proximity of the first engaging material 20.

As seen in FIGS. 1–3, the securment point 16 occurs between the center C and the segment tab portion A. This will provide for the first end 28 of the second strap 14 to be secured between the center section C and the segment tab portion A. As seen in the drawings, this will provide for the second strap 14 to move linearly about the securment point 16. Thereby enabling the second strap 14 to be able to wrap around the first segment tab portion A and the second segment tab portion B. This second strap, as illustrated, is not completely secured to the first or second end of the first strap, so as to offer freedom of movement for the second strap 14.

It is noted that if sewing is used in fabrication process of the male urethral pad of the present invention, the first end 28 of the second strap 14 can be sewn simultaneously with an end of a cotton felt covered inclusion pad. Thereby eliminating extra steps of separately securing the first end 28 of the second strap 14 as well as separately securing each end of the inclusion pad to the inside surface of the first strap. FIG. 3 illustrates the simultaneous securment of an end of the pad and the first end of the second strap.

Secured to the lower surface 32 of the second strap 14 is a cooperating securing means that correspond to the first securing means. As illustrated (see FIG. 1), this second securing means 18 is an interlocking material such as cooperating fabric hook or loop material.

Figure 4A:
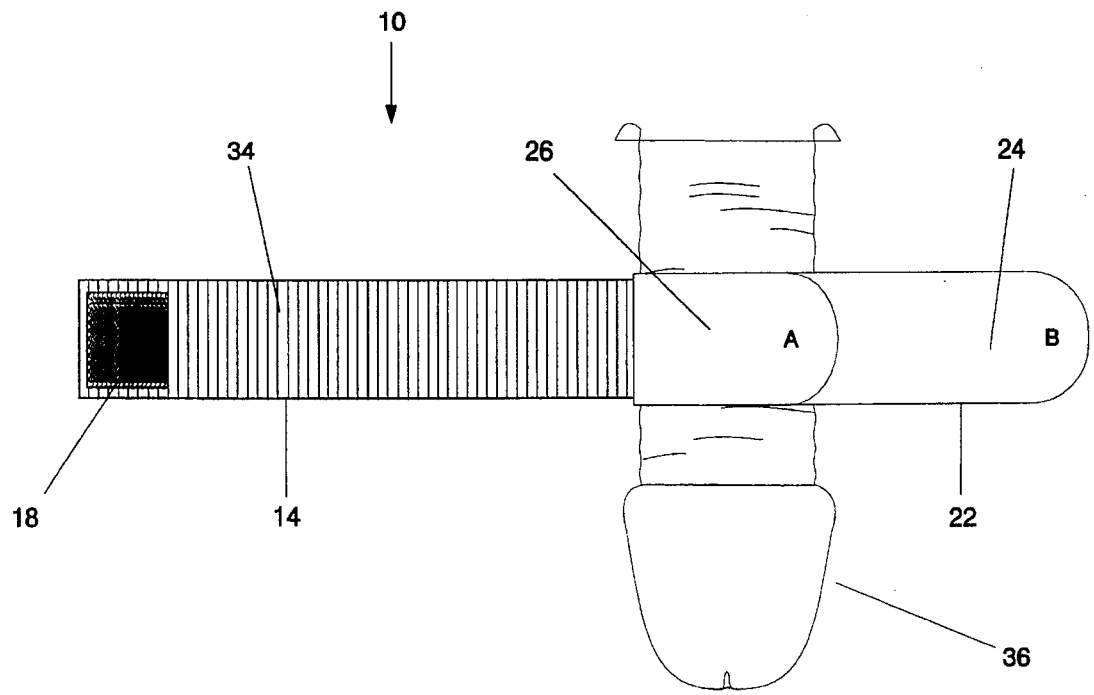
FIG. 4a is a front plan view of the first step for the attachment of the urethral closure pad of the present invention.
Figure 4B:
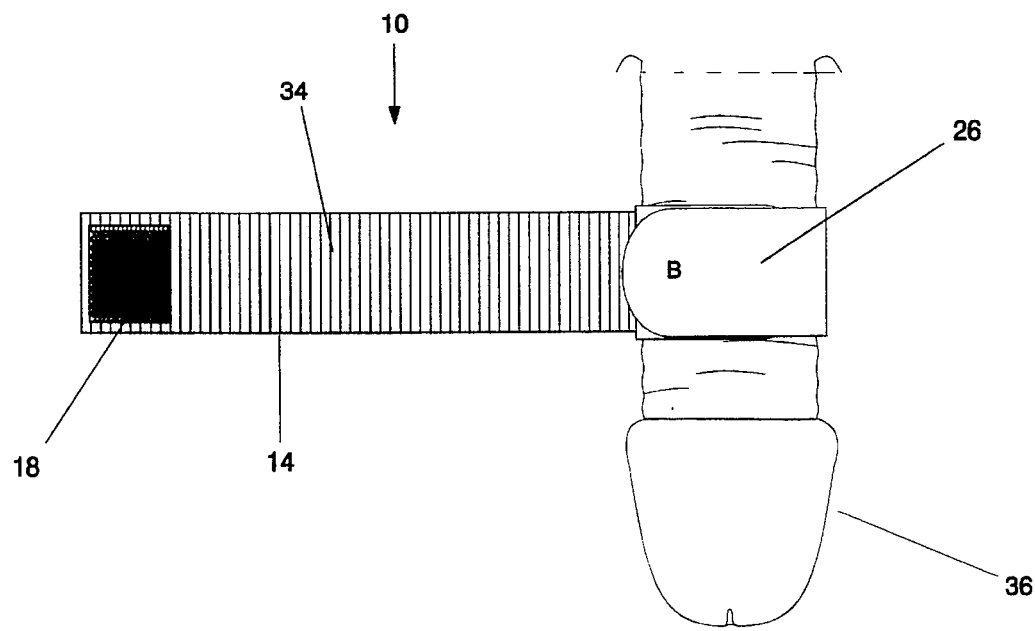
FIG. 4b is a front plan view of the second step for the attachment of the urethral closure pad of the present invention.
Figure 4C:
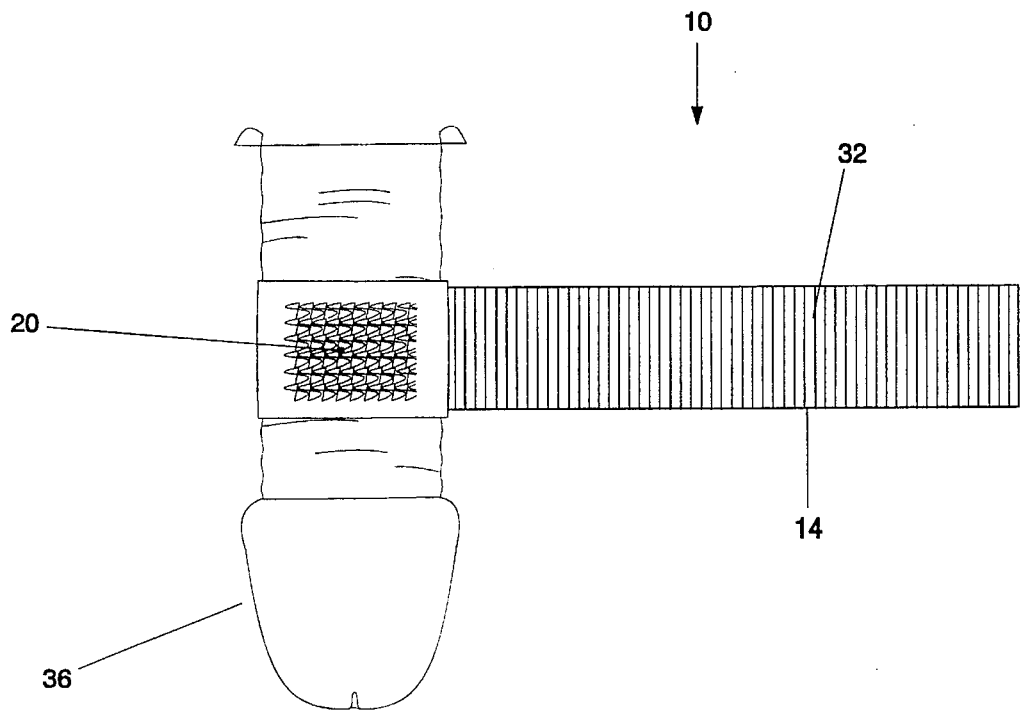
FIG. 4c is a back plan view of the second step for the attachment of the urethral closure pad of the present invention.
Figure 4D:
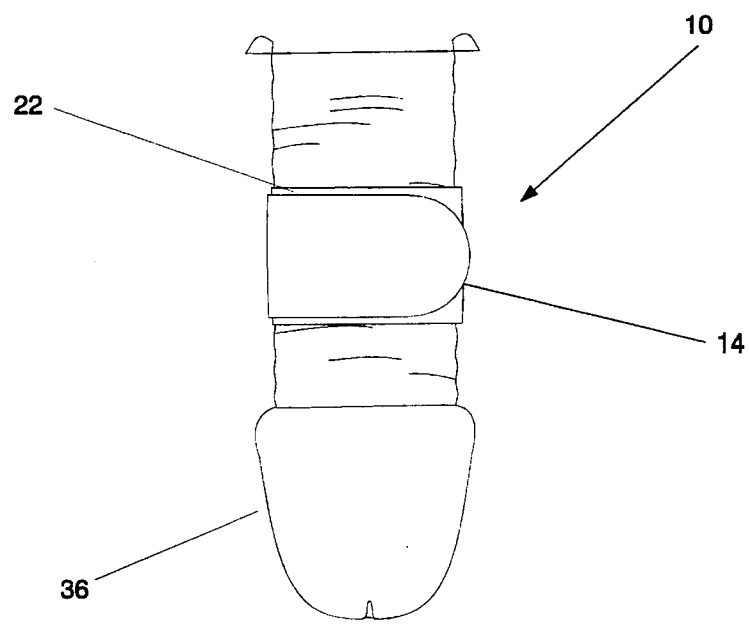
FIG. 4d is a front plan view of the final step for the attachment of the urethral closure pad of the present invention to a penis.

Utilization of the device is illustrated in further detail in FIGS. 4a–4d. FIG. 4a shows the first step that is used in order to attached the urethra closure pad 10 to the user. As seen in this figure the first step is to positioned the urethra closure pad 10 centrally on the under surface of the penis 36. This will provide for the inclusion pad to contact the under surface of the penis and will also render for the inclusion pad to be located under the urethra canal. Once in place, the first end A of the first strap 22 is wrapped around the penis 36. This will provide for the inside surface 24 of the first end A to contact the skin while the outside surface 26 of the first end A is facing the user. The next step, as seen in FIG. 4b is overlap the second end B to the first end A. As seen in the back view in FIG. 4c, this will provide for the hook or loop material 20 to be located under the urethra canal of the penis 36. The last step, as seen in FIG. 4d is to provide for the second strap to be wrapped and stretched over ends A and B. This will provide for the securing means 18 that is located on the top surface 34 of the second strap to engage with the securing means 20 of the first strap. Thereby locking and securing the strap onto the user.

Figure 5:
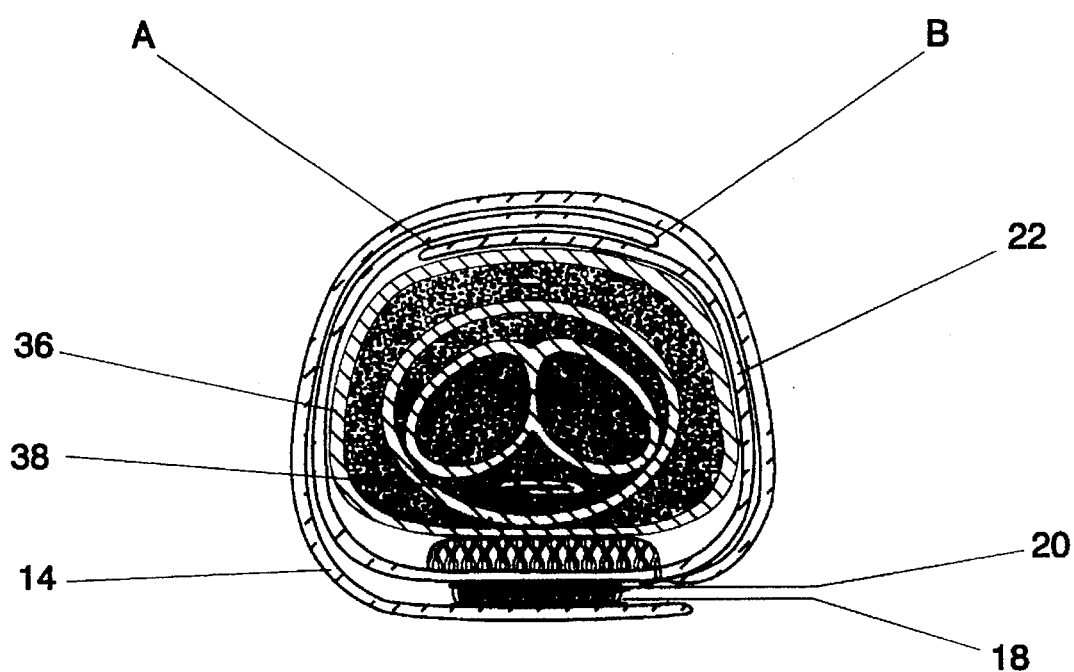
FIG. 5 is a cross sectional view of the urethral closure pad of the present invention secured onto a penis.

A cross sectional view of the strap secured on the user is illustrated in FIG. 5. As seen in this figure, the ends A and B of the first strap 22 are over lapped. The engagement of the cooperating hook and loop material 18 and 20 to each other provides for the device to be secured onto the penis 38. As seen the inclusion pad provides for pressure to be transmitted to the urethra canal 36. Hence, the applied pressure will provide for a device that will close the urethra canal in order to inherently stop the involuntary flow of urine.

The unique design and configuration of the device of present invention permits for the user to customize the male urethral pad without affecting the utility of the device. In order to customize the device 10, the ends A and B of the first strap 22 can be cut accordingly.

While the invention has been particularly shown and described with reference to an embodiment thereof, it will be understood by those skilled in the art that various changes in form and detail may be made without departing from the spirit and scope of the invention.

I claim:

1. A male urethral closure pad comprising:

a first strap having a first end, a center, a second end, an outside surface and an inside surface;

an inclusion pad is centrally affixed at said center to said inside surface of said first strap;

a first securing means is centrally affixed to said outside surface of said first strap to provide for said first securing means to be located on said center of said first strap;

a second strap made from an elastic material includes a first end, a second end, a lower surface and a top surface;

said first end of said second strap is attached at an securment point to said outside surface of said first strap and said securment point is located between said center and said first end of said first strap and said securment point is located in proximity to said center;

said securment point enables said lower surface and said top surface of said second strap to be exposed;

said second strap is linearly moveable about the securment point to enable said second strap to freely wrap around said first end and said second end of said first strap and said second end of said first strap when secured to a penis; and a second securing means is located at said second end on said lower surface of said second strap to provide for said second strap to maintain elasticity and for enabling said second securing means to engage said first securing means for rendering said male urethral closure pad to be removably secured to a user.

2. A male urethral closure pad as in claim 1 wherein said inclusion pad is covered with a soft non-slippery material.

3. A male urethral closure pad as in claim 2 wherein said first securing means is an interlocking material and said second securing means is an interlocking material.

4. A male urethral closure pad as in claim 3 wherein said first strap is fabricated from a group consisting of polyuarethane foam, canvas, cotton, neoprene/vinyl/SBR, or foam neoprene rubber.

5. A male urethral closure pad as in claim 1 wherein said inclusion pad has opposite ends and said opposite ends are beveled.

6. A male urethral closure pad as in claim 1 wherein said first securing means is located directly, centrally, and oppositely from said inclusion pad to provide for said first securing means to be aligned with said inclusion pad.

7. A male urethral closure pad as in claim 1 wherein said inclusion pad is located under an urethra canal of said penis, said first strap is of sufficient length so that said second end of said first strap overlaps said first end of said first strap when said first strap is secured to said penis.

8. A male urethral closure pad as in claim 7 wherein said second strap is of sufficient length and elasticity so that said second end of said second strap can wrap around said first end and said second end of said first strap when said first strap is wrapped around said penis, and said second end of said second strap is removably secured to said first securing means.

9. A male urethral closure pad as in claim 1 wherein said inclusion pad is fabricated from a solid material.

10. A male urethral closure pad comprising:

a first strap having a first end, a center, a second end, an outside surface and an inside surface;

an inclusion pad is centrally affixed at said center to said inside surface of said first strap;

said outside surface of said first strap is reinforced or covered with a bonded napped material;

a second strap made from an elastic material includes a first end, a second end, a lower surface and a top surface;

said first end of said second strap is attached at a securment point to said outside surface of said first strap and said securment point is located between said center and said first end of said first strap and said securment point is located in proximity to said center;

said securment point enables said lower surface and said top surface of said second strap to be exposed;

said second strap is linearly moveable about said securment point to enable said second strap to freely wrap around said first end and said second end of said first strap when secured to a penis; and an interlocking securing means is located at said second end on said lower surface of said second strap to provide for said second strap to maintain elasticity and for enabling said interlocking securing means to engage said said outside surface of said first strap for providing said interlocking securing means to be located directly under and in proximity to said inclusion pad when secured to said penis.

11. A male urethral closure pad as in claim 10 wherein said inclusion pad is covered with a soft non-slippery material.

12. A male urethral closure pad as in claim 11 wherein said first strap is fabricated from a group consisting of polyuarethane foam, canvas, cotton, neoprene/vinyl/SBR, or foam neoprene rubber.

13. A male urethral closure pad as in claim 10 wherein said inclusion pad has opposite ends and said opposite ends are beveled.

14. A male urethral closure pad as in claim 10 wherein said inclusion pad is located under an urethra canal of said penis, said first strap is of sufficient length so that said second end of said first strap overlaps said first end of said first strap when said first strap is secured to said penis.

15. A male urethral closure pad as in claim 14 wherein said second strap is of sufficient length and elasticity so that said second end of said second strap can wrap around said first end and said second end of said first strap when said first strap is wrapped around said penis, and said second end of said second strap is located directly under said inclusion pad when secured to said outside surface of said first strap.

16. A male urethral closure pad as in claim 10 wherein said inclusion pad is fabricated from a solid material.

* * * * *